(12) United States Patent
Fu et al.

(10) Patent No.: US 9,409,842 B1
(45) Date of Patent: Aug. 9, 2016

(54) METHOD FOR PRODUCING REDOX-ACTIVE TI(IV) COORDINATION COMPOUNDS

(71) Applicant: Cristal Inorganic Chemicals Switzerland Ltd, Baar (CH)

(72) Inventors: Guoyi Fu, Ellicott City, MD (US); Malcolm G. Goodman, Bel Air, MD (US)

(*) Notice: Subject to any disclaimer, the term of this patent is extended or adjusted under 35 U.S.C. 154(b) by 0 days.

(21) Appl. No.: 14/685,291

(22) Filed: Apr. 13, 2015

(51) Int. Cl.
| | | |
|---|---|---|
| *C07F 7/28* | (2006.01) | |
| *C07F 5/06* | (2006.01) | |
| *C07C 37/66* | (2006.01) | |
| *C07C 51/41* | (2006.01) | |
| *H01M 8/18* | (2006.01) | |
| *H01M 8/20* | (2006.01) | |

(52) U.S. Cl.
CPC ............... *C07C 37/66* (2013.01); *C07C 51/418* (2013.01); *H01M 8/188* (2013.01); *H01M 8/20* (2013.01); *H01M 2300/0002* (2013.01)

(58) Field of Classification Search
CPC ....... C07C 37/66; C07C 51/418; H01M 8/20; H01M 8/188; C07F 5/06; C07F 7/28; C07F 11/00; C07F 13/00; C07F 15/02
USPC ............................................... 556/54, 55, 56
See application file for complete search history.

(56) References Cited

U.S. PATENT DOCUMENTS

| | | |
|---|---|---|
| 8,691,413 B2 | 4/2014 | Esswein et al. |
| 8,753,761 B2 | 6/2014 | Esswein et al. |
| 2014/0138576 A1 | 5/2014 | Esswein et al. |

OTHER PUBLICATIONS

Magers, Keith D., et al., "Polarographic and Spectroscopic Studies of the Manganese(II), -(III), and -(IV) Complexes Formed by Polyhydroxy Ligands", Inorganic Chemistry, Mar. 1978, pp. 515-523, 17(3), Univ. of California Dept. of Chem., Riverside.

Sofen, Stephen R., et al., "Crystal and Molecular Structures of Tetrakis(catecholato)hafnate(IV) and -cerate(IV). Further Evidence for a Ligand Field Effect in the Structure of Tetrakis(catecholate)uranate(IV)", Inorganic Chemistry, 1979, pp. 1611-1616, 18(6), Univ. of California Dept. of Chem., Berkeley.

Cooper, Stephen R., et al., "Synthetic, Structural, and Physical Studies of Bis(triethylammonium) Tris(catecholato)vanadate(IV), Potassium Bis(catecholato)oxovanadate(IV), and Potassium Tris(catecholato)vanadate(III)", Journal of the American Chemical Society, 1982, pp. 5092-5102, 104, Harvard Univ. Dept. of Chem., Cambridge.

Borgias, Brandan A., et al., "Synthetic, Structural, and Physical Studies of Titanium Complexes of Catechol and 3,5-Di-*tert*-butylcatechol", Inorganic Chemistry, 1984, pp. 1009-1016, 23, Univ. of California Dept. of Chem., Berkeley.

Davies, Julian A., et al., "Electroceramics from Source Materials via Molecular Intermediates: $BaTiO_3$ from $TiO_2$ via $(Ti(catecholate)_3)^{2-}$", Journal of the American Ceramic Society, 1990, pp. 1429-1430, 73(5), Univ. of Toledo Dept. of Chem., Toledo.

Buettner, Katherine M., et al., "Bioinorganic Chemistry of Titanium", Chemical Reviews, 2012, pp. 1863-1881, 112, Yale Univ. Dept. of Chem., New Haven.

*Primary Examiner* — Porfirio Nazario Gonzalez

(57) ABSTRACT

A method for producing an aqueous solution of a redox-active coordination compound of a transition metal which can be used directly as an electrolyte in a flow battery wherein the method comprises reacting a freshly precipitated hydrous transition metal oxide with a chelating agent and a base in an aqueous reaction medium to produce a solution of the corresponding redox-active transition metal coordination compound.

7 Claims, No Drawings

METHOD FOR PRODUCING REDOX-ACTIVE Ti(IV) COORDINATION COMPOUNDS

BACKGROUND OF THE INVENTION

The presently described and claimed inventive concept(s) relate to a method for producing electrolytes for electrochemical energy storage systems, and, more particularly, to a method for producing redox-active Ti(IV) coordination compounds in aqueous solution for use as electrolytes in flow battery systems.

A flow battery is a rechargeable fuel cell in which an electrolyte containing one or more dissolved electroactive elements flows through an electrochemical cell that reversibly converts chemical energy directly to electricity. Modern flow batteries are generally two electrolyte systems in which the two electrolytes, acting as liquid energy carriers, are pumped simultaneously through two half-cells separated by a membrane which comprise the reaction cell. On charging, supplied electrical energy causes a chemical reduction reaction in one electrolyte and an oxidation reaction in the other. A generally thin ion exchange membrane positioned between the half-cells prevents the electrolytes from mixing but allows selected ions to pass through to complete the redox reaction. On discharge the chemical energy contained in the electrolyte is released in the reverse reaction, and electrical energy can be drawn from the electrodes. When in use the electrolytes are continuously pumped in a circuit between reactor and storage tanks.

U.S. Pat. No. 8,753,761 B1 describes aqueous redox flow batteries which comprise metal ligand coordination compounds as a novel class of flow battery materials. Metal ligand coordination compounds, such as those comprising titanium, have been observed to exhibit high solubility, reversible electrochemistry (e.g., rapid electrochemical kinetics) and tunable redox potentials.

Production methods for Ti(IV) coordination compounds that can be used as electrolytes in flow batteries normally involve using precursors, such as, for example, $TiCl_4$, titanium alkoxides, and the like as starting materials. These precursors are reacted with the corresponding complexing agents in water or a solvent. However, these precursor materials are all highly reactive and can be difficult to handle especially at large production scale. In addition, counter ions and by-products (e.g., chloride, alcohols, etc.) that are generated during the production process need to be separated and treated which tends to add significant cost to a commercial production process. Thus, the need exists for an improved more economical method for producing redox-active Ti(IV) coordination compounds of the type which are useful in electrochemical energy storage systems, and particularly in flow battery systems.

SUMMARY OF THE INVENTION

The described and claimed inventive concepts(s) comprise in one embodiment a method for producing redox-active Ti(IV) coordination compounds of the type which are useful in electrochemical energy storage systems, and particularly in flow battery systems. The method comprises according to one embodiment (a) precipitating a soluble titanium salt with a base in an aqueous reaction medium to form freshly precipitated hydrous titanium oxide; (b) separating the freshly precipitated hydrous titanium oxide from the aqueous reaction medium; and (c) reacting the freshly precipitated hydrous titanium oxide with a chelating agent and a base in a second aqueous reaction medium to produce a solution of the corresponding redox-active Ti(VI) coordination compound. The aqueous solution of the corresponding redox-active Ti(VI) coordination compound obtained in step (c) can be deployed directly as an electrolyte in a flow battery.

In certain embodiments the soluble titanium salt in step (a) is selected from $TiOCl_2$ and $TiOSO_4$, and the base in step (a) is selected from NaOH, KOH, and $NH_4OH$.

According to another embodiment, the freshly precipitated hydrous titanium oxide in step (a) can be formed by precipitating a metalloorganic compound of titanium with water. In certain embodiments the metalloorganic compound of titanium is selected from the group consisting essentially of titanium tetraisopropoxide, titanium tetra-n-propoxide, titanium tetra-n-butoxide, titanium tetraethoxide, and titanium tetramethoxide.

The freshly precipitated hydrous titanium oxide in step (b) can be separated by filtration and washing with water, although other convenient separation techniques can also be used with good results.

In an alternate embodiment the method includes the additional steps of (d) crystallizing the corresponding Ti(IV) coordination compound to form a crystalline solid; and (e) separating and recovering the crystalline solid from the aqueous solution by any convenient means, such as, for example, filtration, washing with water or a suitable solvent and drying.

The described and claimed inventive concept(s) comprise lower cost (i.e., more economical) methods for obtaining Ti(IV) coordination compounds in aqueous solution than are currently known in the art without having to manage removal of undesirable counter ions and by-products.

DETAILED DESCRIPTION OF THE INVENTION

The described and claimed inventive concepts(s) comprise in a method for producing redox-active Ti(IV) coordination compounds in aqueous solution which are useful in electrochemical energy storage systems, and particularly in flow battery systems. However, before explaining the inventive concept(s) in detail, it is to be understood that the presently disclosed and claimed inventive concept(s) is not limited in its application to the details of construction and the arrangement of the components or steps or methodologies set forth in the following description or illustrated in the drawings. The results obtainable from the presently disclosed and claimed inventive concept(s) are capable of being achieved, practiced or carried out in various ways. Also, it is to be understood that the phraseology and terminology employed herein is for the purpose of description and should not be regarded as limiting.

Unless otherwise defined herein, technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. For example, the term "hydrous titanium oxide" as used herein is intended to mean and include titanium oxide hydrates and include titanic acid, i.e., any of various amorphous weakly acid substances that are hydrates of titanium dioxide.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles and/or methods disclosed and claimed herein can be made and executed without undue experimentation in light of the present disclosure. While the articles and methods of the presently disclosed and claimed inventive concept(s) have been described in terms of particular embodiments, it will be apparent to those of skill in the art that variations may be applied to the articles and/or methods and in the steps or in the sequence of steps of the method described herein without departing from the concept, spirit and scope of the presently disclosed and claimed inventive concept(s). All such similar substitutes and modifications apparent to those skilled in the art are deemed to be within the spirit, scope and concept of the presently disclosed and claimed inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example, but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first," "second," "third," "fourth," etc.) is solely for the purpose of differentiating between two or more items and is not meant to imply any sequence or order or importance to one item over another or any order of addition, for example.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

The method embraced within the inventive concept(s) described herein begins with first (a) converting a titanium precursor compound(s) to hydrous titanium oxide via precipitation, and then (b) separating the freshly precipitated hydrous titanium oxide from any by-products, such as salts, etc., that may have been introduced into the process from the precursor compound(s). The recovered freshly precipitated hydrous titanium oxide is then reacted in an aqueous medium with a chelating agent and a base which correspond to the desired salt of the titanium coordination compound to be obtained. The hydrous titanium oxide may be prepared, for example, by precipitating a soluble titanium salt, such as $TiOCl_2$, $TiOSO_4$, and the like with a base, such as NaOH, KOH, $NH_4OH$, and the like. Using $TiOCl_2$ as the titanium precursor and NaOH as the base, the precipitation reaction would be as shown in Equation (1) below:

$$TiOCl_2 + 2NaOH + (x-1)H_2O \rightarrow TiO_2 \cdot xH_2O + 2Na^+ + 2Cl^- \quad (1)$$
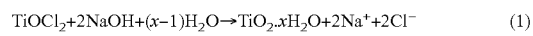

Hydrous titanium oxide may also be produced according to the described and claimed inventive concept(s) by precipitating metalloorganic compounds of titanium with water. Such metalloorganic compounds of titanium are selected from the group consisting essentially of titanium tetraisopropoxide, titanium tetra-n-propoxide, titanium tetra-n-butoxide, titanium tetraethoxide, and titanium tetramethoxide. Using titanium tetra-iso-propoxide by way of an example for the titanium precursor, the precipitation reaction is as shown below in Equation (2):

$$Ti(OPr^i)_4 + (x+2)H_2O \rightarrow TiO_2 \cdot xH_2O + 4Pr^iOH \quad (2)$$
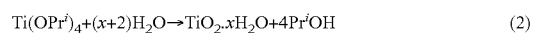

In both reactions (1) and (2), the freshly precipitated hydrous titanium oxide which results may be separated from the reaction by-products (i.e., sodium chloride in the first case and iso-propanol in the second case) by filtration and washing with water. Other convenient methods, such as, for example, centrifugation may also be used with good results.

After washing, the freshly precipitated hydrous titanium oxide may then be used as a titanium precursor to directly react with a chelating agent, such as catechol, pyrogallol, and the like, and a base, such as NaOH or KOH in a second aqueous reaction medium to achieve the desired titanium coordination compounds.

Using the sodium salt of titanium catecholate complex as an example for the chelating agent and NaOH as the base, the reaction will be as shown in Equation (3) below:

$$TiO_2 \cdot xH_2O + 3C_6H_4(OH)_2 + 2NaOH \rightarrow Ti(C_6H_4O_2)_3^{2-} + 2Na^+ + (x+4)H_2O \quad (3)$$
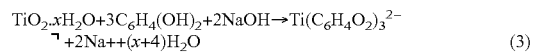

The reaction product is an aqueous solution of a redox-active Ti coordination compound, i.e., the sodium salt of titanium catecholate, which is soluble in water. The aqueous solution can then be used directly as an electrolyte in a flow battery. The concentration of the solution may be adjusted up to 60 wt % as the sodium salt of the complex. If a higher concentration is desired, it can be achieved by removing additional amounts of the solvent (i.e., water) using an evaporator.

Crystalline solids of the Ti(IV) complex may be obtained as an ammonium or a potassium salt. Taking ammonium salt as an example, the reaction will be as shown below in Equation (4):

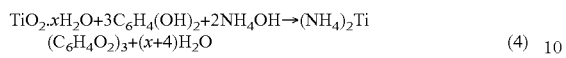

$$TiO_2 \cdot xH_2O + 3C_6H_4(OH)_2 + 2NH_4OH \rightarrow (NH_4)_2Ti(C_6H_4O_2)_3 + (x+4)H_2O \quad (4)$$

The crystalline solids obtained can be separated by filtration, centrifugation, or by other convenient separation methods well known to those skilled in the art.

In the case of $Ti(C_6H_4O_2)_3^{2-}$, which has a high formation constant, the coordination reaction is highly favorable thermodynamically. Freshly precipitated hydrous titanium oxide obtained from the described and claimed inventive concept(s) is relatively active and has relatively high solubility. The coordination reaction may be achieved under ambient temperatures (e.g., at room temperature) or with heating at a somewhat elevated temperature in the range of from 40° C. to 80° C. For other titanium complexes having relatively lower formation constants, mildly heating the reaction medium, from about 60° C. up to the refluxing temperature, would provide enough energy to make the reaction favorable kinetically.

Most notably according to the described and claimed inventive concept(s) is that the coordination reaction is clean and without any by products. The method may be used for synthesizing similar coordination compounds of other transition metals, such as, for example, aluminum, chromium, iron, vanadium, manganese, cerium, and uranium.

EXAMPLES

The following Examples are provided to illustrate certain embodiments described within this disclosure. While each Example is considered to describe specific individual embodiments of the method of preparation and results achieved, none of the Examples should be considered to limit the more general embodiments described herein.

Example 1

Preparation of Titanium Catechol Complex Aqueous Solution (a) Precipitation of Hydrous $TiO_2$ from a $TiOCl_2$ Aqueous Solution
In a beaker, 147.1 g $TiOCl_2$ solution (25.5% in $TiO_2$) with equivalent of 37.5 g (0.47 mol) TiO2 was first added followed by the addition of 300 g of deionized (DI) water with stirring. Then a 20 wt % NaOH solution was added to the aqueous $TiOCl_2$ solution at a rate of about 5 ml/min with sufficient stirring until the pH of the mixture was at 7.0. Stirring was continued for another 15 minutes. A precipitate was produced that was separated by filtration and then the filtrate was washed with DI water a few times, i.e., until the conductivity of the filtrate was at 1 mS/cm or below. The washed precipitate, i.e., freshly precipitated hydrous titanium oxide, is used immediately in the following step for the preparation of titanium catechol complex.

(b) Preparation of Titanium Catechol Complex Solution
The washed precipitate from step (a) above was re-dispersed in DI water in a beaker to a total weight of 500 g. To this hydrous $TiO_2$ dispersion, were added in the sequence, (i) 155.5 g (1.41 mol) catechol, and (ii) 50 g NaOH and DI water until the total weight of the mixture was at 800 g. The mixture was stirred for 8 hours at ambient temperature. A very dark brown and visually transparent solution was obtained. The major FT-IR bands of the aqueous solution matched those published in the literature indicating the desired titanium catechol complex was indeed formed by this synthesis method. UV-Vis spectra showed the characteristic ligand to Ti(IV) charge transfer band centered at 389 nm (Inorg. Chem. 1984, 23, 1009-1016) further confirming the formation of the desired complex.

Example 2

Preparation of Titanium Pyrogallol Complex Aqueous Solution

Precipitated hydrous $TiO_2$ was prepared as described in step (a) in Example 1. However, in the complex preparation step (b), catechol was replaced with an equivalent amount of pyrogallol (1,2,3-trihydroxybenzene).

Example 3

Preparation of Titanium Gallic Acid Complex Aqueous Solution

Precipitated hydrous $TiO_2$ was prepared as described in step (a) in Example 1. However, in the complex preparation step (b), catechol was replaced with an equivalent amount of gallic acid.

Example 4

Preparation of Titanium Catechol Dihydroxynephthalene Complex Aqueous Solution

Precipitated hydrous $TiO_2$ was prepared as described in step (a) in Example 1. However, in the complex preparation step (b), catechol was replaced by a mixture of catechol and dihydroxynephthalene at a ratio of 2:1. The reaction mixture was heated to a temperature of 80° C. and held for 8 hours.

Example 5

Preparation of Titanium Catechol Pyrogallol Complex Aqueous Solution (a) Precipitation of Hydrous $TiO_2$ from $TiOCl_2$ Aqueous Solution
A 235.3 g $TiOCl_2$ solution (25.5% in $TiO_2$) with the equivalent of 60 g $TiO_2$ (0.75 mol) was diluted with 247 g DI water in a 1 L beaker. Separately, 500 g of DI water was prepared in a 2 L reactor/beaker, with stirring. Then the $TiOCl_2$ solution and an NaOH/KOH solution (5M in NaOH and 5M in KOH) were to the reactor at an inflow rate of the $TiOCl_2$ solution of about 10 ml/min simultaneously with sufficient inflow of the NaOH/KOH solution to control the pH of the reaction mixture at 9. After all of the $TiOCl_2$ solution was added, the resulting precipitate was stirred for another 30 min. The precipitate was then filtered, and the filtrate was washed with DI water until the filtrate conductivity was about 1 mS/cm or lower.

(b) Preparation of Titanium Catechol Pyrogallol Complex Aqueous Solution
The fresh precipitate from step (a) was weighed, and DI water was added to achieve a total weight of 500 g. The resulting mixture, i.e., slurry, was then transferred to a 1 L roundbottom flask reactor with heating mantle. In sequence, 165.2 g catechol was added to the flask reactor and then 94.6 g pyrogallol, and then 32 g NaOH and 44.9 g KOH. The reaction mixture was stirred and heated to 70° C. and the temperature was maintained at 70° C. for 8 hours. A very dark brown and visually transparent solution was obtained. UV-Vis spectra showed the characteristic ligand to Ti(IV) charge transfer band centered at 389 nm confirming the formation of the desired complex.

Example 6

Preparation of Titanium Catechol Complex Aqueous Solution (a) Precipitation of Hydrous $TiO_2$ from Titanium Tetra-Iso-Propoxide
In a beaker, 178 g titanium tetra-iso-propoxide (26.7% in $TiO_2$) with an equivalent of 37.5 g (0.47 mol) $TiO_2$ was first mixed with 178 g iso-propanol, and then the resulting reaction mixture was slowly added to a beaker containing 356 g of DI water with stirring. After stirring for 30 minutes, the precipitate thus produced was separated by filtration, and the filtrate was washed with DI water a several times until the conductivity of the filtrate was at 1 mS/cm or lower. The washed fresh precipitate was immediately used in the following step (b) for preparing a titanium catechol complex in aqueous solution.
(b) Preparation of Titanium Catechol Complex Aqueous Solution
The titanium (IV) complex solution was prepared as described in step (b) of Example 1.

Example 7

Preparation of Titanium Catechol Complex Ammonium Salt Crystalline Solid

The preparation is the same as described in Example 1, except that in the "complex preparation step (b)", NaOH was replaced with an equivalent amount of ammonia solution. The complex reaction was carried out at a temperature of 60° C. for 8 hours. After the reaction, the product suspension was cooled to room temperature and left undisturbed overnight. A crystalline solid was obtained which was then separated by filtration, and the filtrate was washed with ethanol several times sufficiently to remove by-product residues. The resulting crystalline solid material was dried in air at room temperature. The crystalline solid was characterized by XRD, FT-IR and UV-Vis spectroscopy. The results were in agreement with corresponding spectroscopic data found in published literature.

Example 8

Preparation of Titanium Catechol Complex Potassium Salt Crystalline Solid

The preparation is the same as described in Example 1, except that in the "complex preparation step (b)", NaOH was replaced with an equivalent amount of KOH. The complex reaction was carried out at 70° C. for 8 hours. After the reaction, the product suspension was cooled to room temperature and left undisturbed overnight. A crystalline solid was obtained which was then separated by filtration, and the filtrate was washed with ethanol several times sufficiently to remove by-product residues. The resulting crystalline solid material was dried in air at room temperature. The crystalline solid was characterized by XRD, FT-IR and UV-Vis spectroscopy. The results were in agreement with the crystalline solid having a formula of $K_4[TiO(C_6H_4O_2)_2]_2 \cdot 9H_2O$ reported in the literature (Inorg. Chem., Vol 23, No. 8, 1009-1016)

As those skilled in the art will appreciate, numerous modifications and variations of the described and claimed inventive concept(s) are possible in light of these teachings, and all such are contemplated hereby. The present invention contemplates and claims those inventions that may result from the combination of features described herein and those of the cited prior art references which complement the features of the present invention.

What is claimed is:

1. A method for producing a redox-active coordination compound of a transition metal selected from the group consisting essentially of titanium, aluminum, chromium, iron, vanadium, manganese, cerium, and uranium which comprises:
    (a) precipitating a soluble salt of the transition metal with a base in an aqueous reaction medium to form freshly precipitated hydrous transition metal oxide;
    (b) separating the freshly precipitated hydrous transition metal oxide from the aqueous reaction medium; and
    (c) reacting the freshly precipitated hydrous transition metal oxide with a chelating agent and a base in a second aqueous reaction medium to produce a solution of the corresponding redox-active transition metal coordination compound.

2. The method of claim 1 wherein the redox-active coordination compound is Ti(IV) and the method comprises:
    (a) precipitating a soluble titanium salt with a base in an aqueous reaction medium to form freshly precipitated hydrous titanium oxide;
    (b) separating the freshly precipitated hydrous titanium oxide from the aqueous reaction medium; and
    (c) reacting the freshly precipitated hydrous titanium oxide with a chelating agent and a base in a second aqueous reaction medium to produce a solution of the corresponding redox-active Ti(IV) coordination compound.

3. The method of claim 2 wherein the freshly precipitated hydrous titanium oxide in step (b) is separated by filtration and washing with water.

4. The method of claim 2 which includes the additional steps of:
    (d) crystallizing the corresponding Ti(IV) coordination compound to form a crystalline solid; and
    (e) separating the crystalline solid from the aqueous solution.

5. The method of claim 2 wherein the soluble titanium salt in step (a) is selected from $TiOCl_2$ and $TiOSO_4$, and the base in step (a) is selected from NaOH, KOH, and $NH_4OH$.

6. A method for producing a Ti(IV) redox-active coordination compound which comprises:
    (a) precipitating a metalloorganic compound of titanium with water to form freshly precipitated hydrous titanium oxide;
    (b) separating the freshly precipitated hydrous titanium oxide from the aqueous reaction medium; and
    (c) reacting the freshly precipitated hydrous titanium oxide with a chelating agent and a base in a second aqueous reaction medium to produce a solution of the corresponding redox-active Ti(IV) coordination compound.

7. The method of claim 6 wherein the metalloorganic compound of titanium is selected from the group consisting essentially of titanium tetraisopropoxide, titanium tetra-n-propoxide, titanium tetra-n-butoxide, titanium tetraethoxide, and titanium tetramethoxide.

* * * * *